United States Patent [19]
Eyal et al.

[11] Patent Number: 6,071,728
[45] Date of Patent: Jun. 6, 2000

[54] PROCESS FOR THE PRODUCTION OF CRYSTALLINE ASPARTIC ACID

[75] Inventors: Aharon M. Eyal; Vitner Asher, both of Jerusalem, Israel; Pierre Cami, Languevoisin, France; Robert Jansen, Vilvoorde, Belgium; Bruno Jarry, Paris, France; Didier Lecomte, Chauny, France; Jean Scott, Roye, France; Thomas Chattaway, Waterloo; Frank Van Lancker, Sint-Amandsberg, both of Belgium

[73] Assignees: Amylum Belgium, N.V., Aaist, Belgium; A. E. Staley Manufacturing Co., Decatur, Ill.

[21] Appl. No.: 09/331,899

[22] PCT Filed: Jan. 8, 1998

[86] PCT No.: PCT/US98/00290

§ 371 Date: Oct. 18, 1999

§ 102(e) Date: Oct. 18, 1999

[87] PCT Pub. No.: WO98/30712

PCT Pub. Date: Jul. 16, 1998

[30] Foreign Application Priority Data

Jan. 9, 1997 [IL] Israel ......................................... 119986

[51] Int. Cl.[7] .......................... C12P 13/20; C07C 227/00; C07C 229/00
[52] U.S. Cl. ............................ 435/109; 562/554; 562/571
[58] Field of Search ............................ 435/109; 562/554, 562/571

[56] References Cited

U.S. PATENT DOCUMENTS

| 5,488,155 | 1/1996 | Brun et al. | 435/109 |
| 5,530,160 | 6/1996 | Nore et al. | 526/571 |
| 5,541,090 | 7/1996 | Sakano et al. | 435/109 |

FOREIGN PATENT DOCUMENTS

| 0 683 231 | 11/1995 | European Pat. Off. . |
| 0 752 476 | 1/1997 | WIPO . |
| WO 97/27312 | 7/1997 | WIPO . |
| WO 98/03468 | 1/1998 | WIPO . |

*Primary Examiner*—Herbert J. Lilling
*Attorney, Agent, or Firm*—Foley & Lardner

[57] ABSTRACT

The invention provides a process for the preparation of aspartic acid via a fermentation process for the preparation of ammonia fumarate, wherein the pH of the fermentation broth is controlled by the addition of a calcium base to produce a calcium fumarate precipitate, characterized in that ammonium fumarate is produced by separating the precipitated calcium fumarate from the fermentation broth, and reacting the same with a reagent selected from ammonia, ammonium carbonate, ammonia in combination with $CO_2$ and mixtures therefore, to form ammonium fumarate and a co-product selected from calcium carbonate and calcium hydroxide, wherein the energy of indirect neutralization of fumaric acid by ammonia serves as the driving force for the conversion of calcium fumarate to the desired ammonium fumarate product and for the regeneration of a calcium base reagent, and wherein diammonium fumarate is enzymatically converted to ammonium aspartate and acidulated to from aspartic acid.

27 Claims, No Drawings

PROCESS FOR THE PRODUCTION OF CRYSTALLINE ASPARTIC ACID

The present invention relates to a process for the production of crystalline aspartic acid.

Aspartic acid is an acidic amino acid with a molecular formula of $HOOCCH_2CH(NH_3)COO$. It is used in products such as the aspartame sweetener and for formation of the biodegradable polymer polyaspartic acid (PAA). The latter could be utilized as a cobuilder or as a sequestrant in detergents, as a super absorbent polymer and in other applications. The biodegradability of PAA is very attractive, and the potential market is large. It strongly depends, however, on the availability of a low cost aspartic acid and a non-contaminating process for the preparation of aspartic acid.

Aspartic acid is usually produced by enzymatic conversion of diammonium fumarate, as disclosed, e.g., in U.S. Pat. No. 3,198,712, corresponding to British Patent 1,004,218, in which there is described and claimed a process for producing L-aspartic acid which comprises mixing *Pseudomonas trifolii* with an aqueous solution containing a fumaric compound selected from the group consisting of fumaric acid and fumarate and an ammonia compound selected from the group consisting of ammonia and ammonium salt, maintaining the resulting mixture at approximately neutral condition whereby L-aspartic acid forms, and recovering L-aspartic acid from said admixture. The diammonium fumarate is usually a product of reacting ammonia and fumaric acid. The latter is a product of converting maleic acid, which, in turn, is a petrochemical product.

U.S. Pat. No. 3,391,059 describes a process wherein microorganisms capable of converting ammonium maleate directly into aspartic acid (or its salt), are isolated. U.S. Pat. No. 4,013,508 describes a process utilizing two different microorganisms. One converts hydrocarbons to fumaric acid, which is then converted by the other to aspartic acid.

The ammonium aspartate formed contains various impurities that could result from the enzyme, the nutrients used, products of said reactions, etc. Currently, it is purified by acidulation through the addition of a stoichiometric amount of a mineral acid, e.g. sulfuric acid, to reach a pH in the range of about the isoelectric point of the aspartic acid. The aspartate ion is converted to aspartic acid in zwitterionic form, which precipitates out of the solution. This solution contains ammonium sulfate as the main component. The presence of the sulfate salt decreases the purity of the precipitating product due to coprecipitation of contaminants, which coprecipitation is induced by the high ionic strength. It also increases the solubility of aspartic acid in the solution, which reduces the yields. Another disadvantage of the process is the consumption of ammonia and sulfuric acid and the formation of a salt that can be used only as a low grade fertilizer (in most cases at the added cost of the energy and equipment needed to crystallize it out of the solution).

U.S. Pat. No. 4,560,653, assigned to W. R. Grace, and WO 9617950 assigned to Mitsubitshi claims a process for preparing L-aspartic acid, wherein a substrate containing fumarate ions is reacted in the presence of an aspartase, the improvement comprising reducing the pH of the aqueous solution resulting from the contact with said aspartase or aspartase-producing microorganism to about 3 to 4 by addition of maleic anhydride, maleic acid or salts thereof, to insolubilize L-aspartic acid while providing maleic acid in the supernatant phase, removing the insoluble L-aspartic acid, isomerization of the maleic acid in the supernatant phase to fumaric acid, adjusting the pH of the supernatant phase to about 8 to 9, and passing the supernatant phase into contact with aspartase or aspartase-producing microoganism.

A further improvement to this idea is suggested in U.S. Pat. No. 5,541,090. The ammonium maleate formed in the acidulation of the ammonium aspartate solution is directly bioconverted to ammonium aspartate. Thus, said patent describes and claims a process for production of L-aspartic acid comprising the steps of (1) contacting (A) an enzyme-containing material having maleate isomerase activity and aspartase activity, or (B) an enzyme-containing material having maleate isomerase activity and an enzyme-containing material having aspartase activity, with a substrate solution containing maleic acid and ammonia, and/or ammonium maleate to form L-aspartic acid, and (2) recovering L-aspartic acid from the reaction solution, characterized by adding maleic anhydride and/or maleic acid to the reaction solution crystallize L-aspartic acid, and (3) recycling the mother liquors as the substrate solution by addition of ammonia.

The process described in U.S. Pat. Nos. 4,560,653 and 5,541,090 and in WO 9617950 solves the problem of ammonia and sulfuric acid consumption and of finding an outlet for ammonium sulfate through acidulation with maleic acid, but has other drawbacks. The aspartic acid is still precipitated from a solution of high ionic strength, which affects its purity. Maleic acid is also found in the crystals. Aspartic acid is left in the mother liquor. It is not lost if the ammonium maleate formed in the mother liquor on such acidulation is fully converted to ammonium fumarate and recycled. That, however, could not be the case, as no outlet is provided for impurities resulting from the biological conversion of fumarate to aspartate, the chemical conversion of maleate to fumarate and from other sources. Rejection of these impurities requires a significant bleed from the mother liquor, which involves product and reagent losses. Moreover, recycling of a solution containing a significant concentration of aspartic acid could inhibit the biological conversion of fumarate to aspartate.

Other patents, e.g., EP 588,674 and U.S. Pat. No. 5,488,155 suggest acidulation of the ammonium aspartate solution with fumaric acid to precipitate aspartic acid and to form ammonium fumarate.

In a later patent, U.S. Pat. No. 5,530,160, the fumaric acid is added in an alcoholic solution. Thus, said patent describes and claims a process for the preparation of L-aspartic acid comprising treating ammonium aspartate using an alcoholic fumaric acid solution according to an added fumaric acid/ammonium aspartate present molar ratio of the order of 0.05 to 0.8, the said alcoholic solution containing of the order of 1 to 15% of its weight of fumaric acid.

Adding fumaric acid to the solution of ammonium aspartate instead of maleic acid avoids the costs and contamination related to converting maleate into fumarate in a solution, which is sent to the conversion of fumarate to aspartate. However, it does not solve all other difficulties related to product purity, losses, and to the slowing down of the bioconversion by the recycled aspartic acid.

In addition to these difficulties these patents suffer from a common drawback. In order to be efficient, they require the use of fumaric acid or maleic acid in acid form and in a relatively pure form. That requirement is not a problem as long as these acids result from a petrochemical process, but make the fermentation route seem practically impossible.

Fumaric acid was produced in the past by fermentation. A calcium base, probably calcium carbonate, was used as a neutralizing agent in the fermentation, which resulted in calcium fumarate. The fumaric acid was recovered from said salt by acidulation with sulfuric acid to form gypsum and fumaric acid. This method suffered from many difficulties. Some of them resulted from the fact that the neutralizing agent, the fermentation product, calcium fumarate, the final product, fumaric acid and the by-product, gypsum, are all of low water solubility, which interferes in separation between reagents, product and by-product and between those and the biomass. Another problem results from the consumption of lime and sulfuric acid and the formation of gypsum to be disposed of. These and other important drawbacks, such as relatively low yield and low productivity in the fermentation, made the fermentation produced fumaric acid more expensive than the petrochemical fumaric acid. The fermentation route was dropped in the forties.

Furthermore, the fermentation route presents major impurities-related problems. Fumaric acid represents, according to prior art, only about 80% of the acids formed in the fermentation. Typically malic acid, succinic acid and alpha ketoglutaric acid as well as glycerol are also formed in the fermentation. In addition, the liquor formed in the fermentation contains non-utilized carbohydrates, mineral anions and cations resulting from the added nutrients, amino acids, proteins, biomass, etc. Considering the difficulties related to the low solubility of the reagents and the products in this fermentation, as described above, one would expect most of these impurities to follow the fumarate into the enzymatic conversion (also referred to as bioconversion), and to end-up in the ammonium aspartate. These would increase even further the difficulties related to crystallization of aspartic acid from the bioconversion-formed ammonium aspartate.

With this state of the art in mind, it was surprisingly found that high yields of aspartic acid recovery in a pure form are feasible without the consumption of a mineral acid, without significant loss of ammonia values and without the formation of significant amounts of by-product salts. Furthermore, it was surprisingly found that that is achievable in a process where the fumarate values result from fermentation of a carbohydrate.

Thus, according to the present invention there is now provided a process for the production of aspartic acid comprising the steps of: (a) forming an aqueous solution containing diammonium fumarate, using per mole of diammonium fumarate about two moles of an ammonia source, a part of which is recycled from a step of the present process; (b) adjusting the composition of an aqueous solution containing diammonium fumarate obtained through a step of the present process to form a solution having a concentration of about 0.5M to about 2M ammonium fumarate and having a pH of about between 7 and 9; (c) enzymatically converting diammonium fumarate in said adjusted aqueous solution into monoammonium aspartate; (d) acidulating a solution containing said monoammonium aspartate by contacting with a cation exchanger which is at least partially in its acid form, at an elevated temperature of at least 50° C., whereby ammonium ions are transferred from said solution to said cation exchanger and protons are transferred from said cation exchanger to said solution thereby forming aspartic acid therein; (e) separating said aspartic acid containing aqueous solution from said ammonium ion-carrying cation exchanger; (f) separating said aspartic acid from said aqueous solution formed in step (e) by methods known per se; (g) regenerating said ammonium ion-carrying cation exchanger back to a cation exchanger which is at least partially in its acid form in a method that forms an ammonia source; (h) separating and reusing said converted cation exchanger in step (d); and (i) separating and reusing said ammonia source in step (a).

Preferably said ammonia source is selected from a group consisting of ammonia, ammonium carbonate and ammonium bicarbonate.

In preferred embodiments of the present invention said aqueous solution containing diammonium fumarate is formed by fermentation and a raw material for said formation in step (a) is a carbohydrate which is used as a raw material for producing said diammonium fumarate. In the first step a carbohydrate-containing medium is fermented by a fumaric acid-producing microorganism. Said fermentation of carbohydrate typically uses microorganisms belonging to the order Mucorales, especially Rhizopus arrhizus, Rhizopus oryzac, Rhizopus nigricans or other related genera. Other microorganisms like Candida may be used alternately. The fermentation medium can contain, in addition to the carbohydrate, nutrients such as nitrogen sources and minerals. Suitable nitrogen sources include such organic and inorganic sources as urea, ammonium chloride, ammonium sulfate, ammonium acetate, ammonium nitrate, ammonium biphosphate, asparagin and protein hydrolysates. Of the foregoing, urea and ammonium sulfate are preferred. The inorganic salts added to the culture media could include sources of phosphate, sulfur, iron magnesium and zinc. Suitable sources of phosphate include monobasic or dibasic sodium phosphate, monobasic or dibasic potassium phosphate, ammonium biphosphate, or mixtures thereof. Suitable inorganic salts employed in the fermentation include zinc sulfate, iron salts such as ferric tartrate or ferric chloride, and magnesium sulfate. Corn steep liquor or biotin may be added for vitamin supply. The fermentation is conducted at a temperature of about 25° C. to about 35° C., preferably at about 33° C. to about 35° C.

Thus, in especially preferred embodiments of the present invention there is provided a process as herein before defined, comprising the steps of: (a) fermenting a carbohydrate-containing medium by means of a fumaric acid producing microorganism, whereby a fumarate containing fermentation liquor is formed; (b) adjusting the composition of an aqueous solution containing diammonium fumarate obtained through a step of the present process to form a solution having a concentration of about 0.5M to about 2M ammonium fumarate and having a pH of about between 7 and 9; (c) enzymatically converting diammonium fumarate into monoammonium aspartate; (d) acidulating a solution containing said monoammonium aspartate by contacting with a cation exchanger which is at least partially in its acid form, at an elevated temperature of at least 50° C., whereby ammonium anions are transferred from said solution to said cation exchanger and protons are transferred from said cation exchanger to said solution forming aspartic acid therein; (e) separating said aspartic acid containing aqueous solution from said ammonium ion-carrying cation exchanger; (f) separating said aspartic acid from said aqueous solution formed in step (e) by methods known per se; (g) regenerating said ammonium ion-carrying cation exchanger with an aqueous solution of monoammonium fumarate, fumaric acid or mixture thereof obtained through a step of the present process, whereby protons are transferred from said solution to said cation exchanger and ammonium ions are transferred from said cation exchanger to said solution to form diammonium fumarate therein; (h) separating said cation exchanger from step (g) which is partially in its acid form and reusing said cation exchanger in step (d); and (i) decomposing said diammonium fumarate from step (g) to form monoammonium fumarate, fumaric acid or a mixture thereof and to form an ammonia source and reusing said decomposition products.

Fungi can grow satisfactorily in acidic conditions. However, as the build-up of fumaric acid in the fermentation medium has a negative effect on the fermentation, the latter is typically conducted at a slightly acidic pH, from about 4 to 7. Typically a base is directly added as a neutralizing agent and a fumarate salt is formed. Usually the neutral salt of fumaric acid is formed rather than the acidic salt. Said neutralizing agent can be selected from a group consisting of ammonia and hydroxides, carbonates or bicarbonates of ammonium, alkali and alkaline earth metals. Most preferably calcium carbonate is used as a neutralizing agent and calcium fumarate is formed.

In preferred embodiments of the present invention, the carbohydrate is selected from the group consisting of dextrose, preferably produced from cereal starch, including low-grade wheat starch fractions and molasses.

Alternatively, the fumaric acid is continuously removed from the fermentation medium, e.g. by binding to a water immiscible liquid or solid basic extractant or adsorbent. For that purpose one can use a basic extractant, e.g. of the type containing a long chain amine, or a basic resin such as the anion exchangers that carry non-quaternary amine functions or pyridine based resins. Preferably the anion exchanger is a relatively strong one, most preferably of a pKa higher than 5. The fumaric acid can be recovered from said extractant or adsorbent by contacting with a basic solution which consumes a base and forms the fumarate salt. This use of a base will further be referred to as indirect neutralization, it being realized that a base can be used directly or indirectly as a neutralizing agent in said fermentation. The base for that purpose is preferably selected from the group consisting of ammonia and hydroxides, carbonates and bicarbonates of ammonium, alkali and alkaline earth metals. Most preferably this base is ammonia.

Ammonium fumarate is enzymatically converted to ammonium aspartate. Usually the conversion is conducted in a slightly basic medium so that diammonium fumarate is the substrate. Ammonium fumarate formed in fermentation could be fed to said enzymatic conversion. (As used herein, if not defined specifically, the term ammonium fumarate is intended to denote monoammonium fumarate, diammonium fumarate, or a combination thereof) In those cases where the fermentation results in another fumarate salt, as in the case of the preferred embodiment where calcium carbonate is the neutralizing agent and calcium fumarate is the product, this salt is converted to ammonium fumarate. This is preferably effected by a direct or an indirect reaction with ammonia, ammonium carbonate or ammonium bicarbonate.

A most preferred embodiment is described in Israel specification 116,849, the teachings of which are incorporated herein by reference. Precipitated calcium fumarate formed in the fermentation is separated from the fermentation liquor, washed, suspended in water or in an aqueous solution from a previous step and dissolved at an elevated temperature. The calcium fumarate solution can be purified, if needed, by methods such as membrane filtration, ion-exchange, active carbon treatment, solvent extraction, etc. Then it is preferably recrystallized. After recrystallization it is reacted with ammonia and $CO_2$ or with ammonium carbonate or bicarbonate or mixtures thereof. Preferably the pH in the reaction medium is first adjusted to between about 10 and 11. High temperatures and high $CO_2$ pressures are not required. In the reaction, calcium fumarate is converted to ammonium fumarate. The amount of water in the reaction is adjusted so that the ammonium fumarate formed will be quite concentrated, preferably greater than 10% and even more preferred higher than 13%. Calcium carbonate is formed as a by-product, separated from the ammonium fumarate solution and reused as a neutralizing agent, in carbohydrates fermentation to fumaric acid. Preferably the calcium carbonate is calcined prior to the recycle to fermentation, whereby biomass left in it is removed. In a most preferred embodiment the calcined calcium base is quenched in water and kept suspended in the water until reused. This suspension in water helps in removing ashes left from biomass burning and other ashes left from the previous fermentation step.

In a preferred embodiment the ammonium fumarate directly formed in the fermentation or indirectly through conversion of another fumarate salt formed in the fermentation, is purified prior to the enzymatic conversion to ammonium aspartate. Purification can be conducted in known methods such as recrystallization, membrane filtration, ion-exchange, active carbon treatment, solvent extraction, etc.

In another preferred embodiment, ammonium fumarate is purified through a reaction with a calcium compound whereby calcium fumarate forms. Said calcium fumarate is crystallized and, if desired, recrystallized and purified by other known means. It is then converted back to ammonium fumarate by means described above. In a further preferred embodiment the calcium compound is a calcium base selected from the group consisting of calcium oxide, hydroxide, carbonate and bicarbonate. In a most preferred embodiment said calcium base is obtained from calcium carbonate recycled from conversion of calcium fumarate to ammonium fumarate.

As stated, the ammonium fumarate is converted to ammonium aspartate in an enzymatically catalyzed reaction. Typically, most of the ammonium aspartate is monoammonium aspartate, but a small fraction could be in diammonium aspartate form. The term ammonium aspartate as used herein, is intended to denote both monoammonium aspartate and its mixtures with diammonium aspartate, unless otherwise indicated.

The enzymatic reaction is catalyzed by the enzyme aspartase. This enzyme can be produced from many microorganism, including E.coli, Brevibacterium sp, Pseudomonas sp. cultivated in a suitable medium. The ammonium aspartate formation can be obtained by contacting the ammonium fumarate solution directly with the bacterial culture or with permeabilized cells, crude cell extracts, or purified aspartase. When bacterial culture is used directly, the method described in French Patent Publication No. 2,197,979 (1972) can be employed. Cell culture, cells, cell extracts or enzyme itself can be used directly or as immobilized preparations. Examples of immobilized preparations are obtained by immobilizing the cells, cell extracts or enzyme on supports, carriers or bases such as polyacrylamide gels, sulfur-containing polysaccharide (e.g. carrageenan, furcellaran, etc.), gel, collagen gel, alginic acid gel, polyvinyl alcohol gel, agar gel, resins and the like.

The ammonium fumarate concentration in the feed to the conversion is typically from about 0.5M to about 2M. It is usually preferable to add a divalent metal ion such as calcium ion, magnesium ion, manganese ion, strontium ion or the like to the reaction system to improve the enzyme stability. The amount of the divalent ion can be about 0.1 to 10 mM. The reaction is conducted at temperatures of from about 20° C. to 60° C., and the pH is preferably between 7 to 9. The yield of conversion is typically 90% to 100%.

The pKa's of aspartic acid are 1.88, 3.65 and 9.60, and its isoelectric point (pI) is 2.77. The aspartate-containing solution obtained in the conversion is about neutral or even slightly basic. At these conditions both carboxylic functions are negatively charged. One of them is balanced by the positively-charged ammonium group and the other by a cation, ammonium in most cases. This solution is acidulated through contact with a cation exchanger, the functional groups of which are at least partially in proton form. Due to the contact, cation exchange is effected, cations from the solution are adsorbed and protons are transferred from the cation exchanger to the solution, lowering its pH. Those protons react with at least one of the carboxylic groups on the aspartate (the one related to the pKa of 3.65) to form the zwitterion.

The solubility of the aspartic acid in the zwitterion form is low and its crystallization in the cation exchanger could damage the resin and interfere with its operation. Temperature elevation does not always solve the problem. Firstly, it is limited by the thermal stability of the resin and secondly the conditions within the resin pores are different from those in the free solution. Thus, according to JP94017346, in the case of contacting a solution-containing glutamic acid with a cation exchange resin, urea was added to avoid such crystallization. It was found that, in the case of the present process, acidulation by a cation exchanger can be effected without any significant problem resulting from crystallization of aspartic acid in the resin.

The acidulated solution is separated from the ammonium ion-carrying cation exchanger and the latter is sent to regeneration in contact with an acidic solution. The separation is preferably effected without cooling the solution much below the temperature of the acidulation step.

Aspartic acid is separated from the aspartic acid-containing aqueous solution formed on contact with the cation exchanger by known methods. Preferably this separation is effected by crystallization, e.g. by cooling and/or by water evaporation, or solvent addition.

The present process provides a possibility of high yield recovery of aspartic acid from the mother liquor by an additional step. In contacting this mother liquor with a strong acid cation exchanger, aspartic acid obtains an additional proton from the cation exchanger and transforms into the cationic form. As such it is efficiently bound from the mother liquor.

Thus, in a preferred embodiment, a strong acid cation exchanger in its acid form is contacted with the mother liquor of aspartic acid crystallization. The aspartic acid contained in that mother liquor is adsorbed. The aspartic acid carrying cation exchanger resulting from that step is contacted with a solution of the aspartate salt obtained in the conversion step. As a result, the cation of the aspartate salt is bound on the resin and the adsorbed aspartic acid is released into the solution. The latter is separated and sent to aspartic acid crystallization or to further acidulation and the cation exchanger is regenerated by a regenerating acidic solution. Said acidic solution is preferably containing a solute selected from the group consisting of fumaric acid, monoammonium fumarate and mixtures thereof. More preferably, said solution is obtained in another step of the present process.

Losses, as in present industrial practice, or undesired recycling of aspartic acid to the conversion reaction, as suggested in U.S. Pat. Nos. 4,560,653; 5,541,090; 5,488,155; 5,530,160; EP 588,674 WO 9617950 are avoided. As a result, there is no need to push the conditions in the crystallization step to maximum yield. The conditions there can be adjusted to those ensuring the highest product yield. In addition, if required, the bioconversion step could be operated at a relatively low salt concentration, if preferred for higher stability and/or reactivity of the enzyme in the medium, without losing in the overall recovery yield.

Use of a sequence of a weak acid cation exchanger and a strong acid cation exchanger could be preferred in some circumstances. In that case, the aqueous solution containing the aspartate salt obtained in the bio-conversion reaction is first contacted with the weak acid cation exchanger, and the resulting solution is contacted with the strong acid cation exchanger resulting from the contact with the mother liquor. The aqueous solution obtained in that contact, is sent to the aspartic acid crystallization. Regeneration of the resins is done in the following sequence: the regeneration acidic solution is first contacted with the strong acid cation exchanger and then with the weak one. This way no significant excess of regenerating acidic solution is needed.

The free mother liquor obtained contains most of the impurities resulting from the various sources. As it is essentially aspartic acid free, there is no need to recycle it to the enzymatic conversion (directly or indirectly). Therefore, recycle of impurities and their build-up in the system are avoided.

The ammonium ion-carrying cation exchanger, formed in the ammonium aspartate acidulation step, is regenerated to its at least partial acid form for reuse, in a method wherein an ammonia source is formed. That ammonia source is preferably selected from the group consisting of ammonia, ammonium carbonate and ammonium bicarbonate. Regeneration methods forming acidic or neutral ammonium salts of a mineral acid are preferably avoided. Thus, treatment with a strong mineral acid, such as sulfuric acid, forms neutral ammonium salts of said acid, e.g. ammonium sulfate which is not desired in the process apart from a small amount in fermentation and should be avoided or limited.

In a preferred embodiment the ammonium ion-carrying cation exchanger is treated with $CO_2$ as a reagent, preferably under pressure. A solution of ammonium carbonate or bicarbonate or mixtures thereof is formed as an ammonia source for reuse. Such a solution could be reused as such or after treatments such as concentration or distillation. Said distillation forms ammonia or ammonia mixtures with $CO_2$ and optionally also water vapors. Those could then be used as ammonia sources.

The cation exchanger used for acidulating ammonium aspartate is preferably of a weak acid or a medium acid properties. Strong acid cation exchangers, e.g. of the sulfonate type, are preferably avoided as their conversion back to the partially acidic form requires relatively strong acid. Yet, according to one of the preferred embodiments of this invention, fumaric acid is formed. This fumaric acid can be used for that purpose as well as for the regeneration of a strong acid cation used for recovery of aspartic acid from crystallization mother liquor.

Alternatively, to the use of $CO_2$ as a reagent for regenerating the cation exchanger, one could use a solution containing monoammonium fumarate, fumaric acid or mixtures thereof, whereby protons are transferred from said solution to the cation exchanger and ammonium ions are transferred from said cation exchanger to said solution to form diammonium fumarate therein.

Monoammonium fumarate, fumaric acid or a mixture thereof for regeneration of said ammonium-carrying cation exchanger are obtained by decomposition of diammonium fumarate in a method which also forms an ammonia base.

According to a preferred embodiment the diammonium fumarate resulting from fermentation is decomposed. According to another preferred embodiment, diammonium fumarate formed in said regeneration step is decomposed.

According to one preferred embodiment, diammonium fumarate resulting from fermentation is fed after adjustment to the enzymatic conversion. According to another preferred embodiment, diammonium fumarate formed in said regeneration step is fed after adjustment to the enzymatic conversion. Said adjustment could consist of steps such as adjusting the concentration and pH and adding components, as needed, e.g. a salt of a bivalent metal, in the enzymatic conversion step.

Such adjustment could also consist of a purification step by known methods such as recrystallization, membrane filtration, membrane dialysis or electrodialysis, ion exchange, active carbon treatment, solvent extraction, etc. In a preferred embodiment said decomposition to monoammonium fumarate and an ammonium base serves as a purification means. Monoammonium fumarate is crystallized out of the solution in a rather pure form. It can be further purified, if needed, e.g. by recrystallization. In a further preferred embodiment this purified monoammonium fumarate is converted to diammonium fumarate by contacting with ammonium ion-carrying cation exchanger, e.g. that formed on acidulation of ammonium aspartate, preferably after washing, the diammonium fumarate solution formed is fed, after adjustment to said enzymatic conversion.

In another preferred embodiment ammonium fumarate is purified through a reaction with a calcium compound, whereby calcium fumarate forms. Said calcium fumarate is crystallized and, if desired, recrystallized and purified by other known means. Then said calcium fumarate is converted back to ammonium fumarate by means described above. In a further preferred embodiment the calcium compound is a calcium base selected from a group consisting of calcium oxide, hydroxide, carbonate and bicarbonate. In a most preferred embodiment said calcium base is obtained from calcium carbonate which is recycled from conversion of calcium fumarate to ammonium fumarate.

Said decomposition of diammonium fumarate is preferably effected by at least one method selected from a group consisting of:

(i) electrodialytic water splitting;

(ii) contacting with an extractant under $CO_2$ pressure, whereby fumaric acid is extracted;

(iii) contacting with a cation exchanger which is at least partially in its acid form, whereby ammonium ions are transferred from the solution to the cation exchanger forming ammonium ion-carrying cation exchanger and protons are transferred from the cation exchanger to the solution forming monoammonium fumarate therein; and (iv) thermal decomposition.

Electrodialytic water splitting is effected by a device containing charged membranes including bipolar membranes and uses electric energy as a driving force. It could split diammonium fumarate to ammonia and fumaric acid and/or monoammonium fumarate. The ammonia is obtained as relatively concentrated solution and could be used as such or after distillation as an ammonia source. In most cases monoammonium fumarate will be preferred as the other product due to its higher solubility, avoiding the risk of crystallines that could interfere with the operation of the bipolar membrane.

Contacting an aqueous solution of diammonium fumarate with a suitable water immiscible base under $CO_2$ pressure results in binding of fumaric acid to said base and formation of ammonium carbonate or bicarbonate. Such water immiscible base is selected from a group consisting of extractants and basic solid adsorbents Suitable extractants contain high molecular weight amines with a total number of carbon atoms of at least 18. Preferably those are aliphatic secondary or tertiary amines. The amine is dissolved in a solvent or a mixture of solvents. Preferably such solvent contains an alkanol acting as an extraction enhancer. Basic solid adsorbents are anion exchangers carrying non-quaternary amine groups or pyridine-based resins. The bound fumaric acid can be stripped by washing with water at an elevated temperature, preferably close to or above 100° C. In case of relatively strong water immiscible base, complete stripping of the bound acid may require large volumes of water and thus end up with dilute fumaric acid solution. Alternatively, the fumaric acid-loaded base is stripped with an aqueous solution of diammonium fumarate. Fumaric acid transfers to said solution forming monoammonium fumarate therein. In a preferred embodiment, monoammonium fumarate is crystallized out of the solution formed and the remaining solution is reused to form a diammonium fumarate containing stripping solution. In another preferred embodiment the contact under $CO_2$ and stripping with water and/or an aqueous solution of diammonium fumarate are conducted in a counter current mode. In yet another preferred embodiment, a part of the bound fumaric acid is stripped by water and then another part of it is stripped with an aqueous solution of diammonium fumarate.

Alternatively, an aqueous solution of diammonium fumarate is acidulated by contacting with a cation exchanger, which is at least partially in its acid form. Ammonium ions transfer from said aqueous solution to the cation exchanger and protons transfer from said cation exchanger to the solution forming monoammonium fumarate therein. The solution is separated from the ammonium ion-carrying cation exchanger, which is regenerated by transformation back to the at least partially acid form, preferably after first washing with water or an aqueous solution. Preferably this regeneration is effected by water under $CO_2$ pressure. An aqueous solution containing ammonium bicarbonate, carbonate or a mixture thereof, is formed and is used as an ammonia source. In a preferred embodiment said separated aqueous solution is treated for the separation of monoammonium fumarate therefrom, preferably by crystallization. The remaining solution is preferably used to reconstitute an aqueous solution of diammonium fumarate for further decomposition to an ammonia source and monoammonium fumarate or fumaric acid.

In another alternative procedure, diammonium fumarate is thermally decomposed into ammonia and monoammonium fumarate. Heating of solid diammonium fumarate or a solution thereof to a temperature of above 100° C. and more preferably to above 150° C. results in removal of ammonia to the vapor phase and in the conversion of at least part of the diammonium fumarate to monoammonium fumarate. Said ammonia is recovered and used as an ammonia source. In a preferred embodiment said monoammonium fumarate is separated from the decomposition product, preferable by crystallization. The rest of the decomposition product is preferably used to reconstitute a diammonium fumarate feed for further decomposition to an ammonia source and monoammonium fumarate or fumaric acid.

The cation exchanger used for acidulation of diammonium fumarate is selected from a group consisting of weak or medium acid strength cation exchangers. It could be the same cation exchanger used for the acidulation of ammonium aspartate or of similar acidity. Preferably it is somewhat less acidic.

In a preferred embodiment an aqueous solution containing monoammonium fumarate formed by decomposition of diammonium fumarate is contacted with a suitable water immiscible base. This contact disproportionates diammonium fumarate by binding fumaric acid to the water immiscible base, which converts monoammonium fumarate into diammonium fumarate. Such water immiscible base is selected from a group consisting of extractants and basic solid adsorbents. Suitable extractant contain high molecular weight amines with a total number of carbon atoms of at least 18. Preferably those are aliphatic secondary or primary amines. The amine is dissolved in a solvent or a mixture of solvents. Preferably, such solvent contains an alkanol acting as an extraction enhancer. Basic solid adsorbents are anion exchangers carrying non-quatenary amine groups, or pyridine-based resins. The water immiscible base could be similar to that used in decomposition of diammonium fumarate under $CO_2$ pressure or of a similar basicity. Preferably it is somewhat weaker. The bound fumaric acid can be stripped by washing with water at an elevated temperature, preferably close to or about 100° C. Alternatively, a combination of stripping with water and with a diammonium fumarate solution is effected as suggested above. In a preferred embodiment the contact with the monoammonium fumarate and stripping with water are conducted in a counter current mode.

Thus, electrodialytic water splitting, contact with a water immiscible base under $CO_2$ pressure, thermal decomposition, and acidulation by contact with a cation exchanger, which is at least partially in acid form, or a combination thereof, result in decomposition of diammonium fumarate to an ammonia source, which is ammonia, ammonium carbonate, ammonium bicarbonate or mixture thereof, and in fumaric acid, monoammonium fumarate or a combination thereof. The ammonia source is used as a neutralizing agent in the fermentation or for converting a fumarate formed in said fermentation into ammonium fumarate. The monoammonium fumarate or fumaric acid is used to regenerate ammonium ion-carrying cation exchangers formed in the acidulation of ammonium aspartate or by the recovery of aspartic acid from a mother liquor formed on crystallizing aspartic acid. In those cases where monoammonium fumarate is formed, it is preferably crystallized out of solutions containing it and more preferably recrystallized as a means of purification.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

5 Kg. of fermentation broth analyzed and was found to contain: 329 g (2.84 mole) fumarate, 39.5 g (0.29 mole) maleate, 24 g (0.20 mole) succinate, 20.5 g (0.14 mole) alpha ketoglutarate and 76.5 g (0.83 mole) glycerol. The broth was filtered and the solids were washed with water to form 1.42 Kg of wet cake containing: 283 g (2.44 mole) fumarate, 4.2 g (0.031 mole) maleate, 8.8 g (0.074 mole) succinate, <9 g (<0.062 mole) alpha ketoglutarate and <3 g (<0.032 mole) glycerol.

The 1.42 Kg. wet cake was re-suspended in 1.5 Kg de-ionized water at 30° C. and 344 g of a 33% ammonia solution was added. Gaseous CO2 was then bubbled through the suspension until the pH was 8.7. After cooling the ambient temperature the suspension was filtered and the cake was washed with 1.2 Kg. water. The wash water was combined with the filtrate. The composition of the combined solution was 257 g (2.21 mole) fumarate (>90% conversion), 2.2 g. (0.016 mole) maleate, 8.2 g. (0.069 mole) succinate, 0.4 g (0.003 mole) alpha ketoglutarate 0.18 g (0.0045 mole) calcium and 90 g (5 mole) ammonia.

These results show that high conversion yields can be combined with a substantial purification of the fumarate. The proportion of the fumarate in the total fermentation products increased from 67% in the broth to 96% in the product ammonium fumarate.

EXAMPLE 2

21.8 g of an aqueous solution containing 1.74 M (NH4)2Fu were shaken with 1.37 g of a weak acid cation exchanger (WACE) HP336 in its acid form for 3 hours at 85° C. The resin was separated and the remaining aqueous solution was analyzed. 20% of its initial (NH4)2Fu was coverted to NH4HFu. The effective ion exchange capacity of the WACE in this exchange was about 5.5 equ/g of dry resin.

EXAMPLE 3

(a) 70 g of an extractant were contaced in a pressure vessel with 70 g of an aqueous phase under CO2 pressure of 27 atm. The composition of the organic phase was 1.2M Alamine 336 (Henkel) and 20% octanol in kerosene. The aqueous phase was a 25.5% (NH4)2Fu solution. After an overnight mixing the phases were separated and analyzed. The organic phase contained 0.24 equ. of fumaric acid per mole of amine in the extractant.

(b) The experiment in (a) was repeated with an extractant containing 0.6M of the same amine, 3.45 of octanol and 43% of isopropanol in kerosene. The aqueous phase was 20% (NH4)2Fu. After contact and phase separation, the organic phase contained 0.41 equ. of fumaric acid per mole of amine in the extractant.

(c) The experiment in (a) was repeated with an extractant composed as in (b) and an aqueous solution containing 6.6% NH4HFu. After contact and phase separation, the organic phase contained 0.98 equ. of fumaric acid per mole of amine in the extractant.

(d) The experiment in (a) was repeated with an extractant composed as in (b) and an aqueous solution containing 11.2% NH4HFu. After contact and phase separation, the organic phase contained 1.45 equ. of fumaric acid per mole of amine in the extractant.

EXAMPLE 4

125 g octanol were placed in a beaker and heated to 170° C. 40 g of an aqueous solution containing 2.5M(NH4)2Fu were added in drops to the hot octanol during 2 hours. Heating was continued for additional 45 minutes and then stopped. The crystals formed were separated, washed with ethanol and dried. 0.5 g of the dry crystals were dissolved in 10 g water. The pH of the solution was 3.45, slightly lowever than that of NH4HFu solution of the same concentration.

EXAMPLE 5

An extractant composed of 40% Alamine 336 and 6% octanol in kerosene and containing 1.4N fumaric acid was washed with water at 95° C. in 6 stages of a counter current mode. Practically all the fumaric acid was washed out forming an aqueous solution of 0.1N. On cooling this solution to 25° C. fumaric acid crystallizes out.

EXAMPLE 6

50 g Reillex resin carrying 2.75 eq/g of fumaric acid was mixed at 75° C. with 50 g of an aqueous solution containing 14.1% (NH4)2Fu. After 3 hours the aqueous phase was analyzed. 16% Of its (NH4)2Fu was coverted to NH4HFu and the corresponding equivalents of resin sites were converted from their fumaric acid carrying form to their free base form.

EXAMPLE 7

An aqueous solution containing 4.2% NH4HFu and 12.7% (NH4)2Fu at 75° C. was cooled slowly. The NH4HFu crystals formed were filtered, washed with cold water, dried in an oven at 70° C. and weighed. The monoammonium fumarate crystallization yield found was 96%.

EXAMPLE 8

A 10 liter sterile solution containing 1270 g dextrose, 17.5 g $(NH_4)_2SO_4$, 4 g $MgSO_4.7H_2O$, 3 g $KH_2PO_4$, 0.5 g $ZnSO_4.7H_2O$, 0.1 g $FeCl_3.6H_2O$, 5 g corn steep liquor and 960 g of $CaCO_3$ in suspension is fermented at 34° C. using Rhizopus arrhizus strain NRRL 1526.

After 54 hours of fermentation 800 g of fumaric acid is produced as calcium salt.

The broth is filtered to get a cake of the mycelium and calcium fumarate which is washed with 2 liters of cold water. The washed cake contains 720 g of fumaric acid as its calcium salt.

The cake is suspended in 12 liters of boiling water with agitation for one hour and then filtered at 95° C. to obtain a calcium fumarate solution.

Calcium fumarate is crystallized by cooling the filtrate at 10° C. for 2 hours.

The calcium fumarate is filtered, washed in 1 liter of cold water and dried to obtain 850 g of calcium fumarate, with a purity higher than 90%.

790 g of this calcium fumarate is suspended in 4.5 liters of 180 g ammonia water solution and $CO_2$ is bubbled until the pH reaches 8.5. Calcium carbonate precipitate is filtered and washed in cold water. 4.5 liters of diammonium fumarate solution containing 540 g of fumaric acid is obtained.

This solution, heated to 75° C., is acidulated by percolating on a 5 liter cation exchange column obtained in a previous step. The column is then washed with 3 liters of water and named column A. Column A was treated by water under $CO_2$ pressure of 10 bar. More than 50% of the ammonium ions bound to it in the acidulation step were obtained in the $CO_2$ containing water.

Five liters of the acidulated effluent containing 500 g of fumaric acid, mainly as monoammonium fumarate, is concentrated under reduced pressure at 70° C. to obtain 2 liters of condensate. After cooling for 2 hours at 10° C., monoammonium fumarate crystallizes with 99% purity.

The crystals are separated by filtration and dissolved in water at 75° C. The solution is percolated on a 2 liter column B, containing a cation exchanger carrying ammonium ions obtained from a previous step of acidulating ammonium aspartate. A 1.5 liter solution is formed, containing 180 g of fumaric acid in its diammonium fumarate form. The cation exchanger is practically completely regenerated to its acid form.

The pH of the diammonium fumarate solution is adjusted to 8. By means of the bacterium Pseudomonas fluorescens strain ATCC 21973, it is converted, at 58° C., to monoammonium aspartate solution at a molecular yield higher than 95%.

The solution of the monoammonium aspartate is heated to 75° C. and acidulated by percolating on column B. On cooling the effluent to 10° C., more than 85% of its aspartic acid content crystallized as pure aspartic acid.

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

What is claimed is:

1. A process for the production of aspartic acid, comprising the steps of:
   (a) forming an aqueous solution containing diammonium fumarate, using per mole of diammonium fumarate about two moles of an ammonia source, a part of which is recycled from a step of the present process;
   (b) adjusting the composition of an aqueous solution containing diammonium fumarate obtained through a step of the present process to form a solution having a concentration of about 0.5M to about 2M ammonium fumarate and having a pH of about between 7 and 9;
   (c) enzymatically converting diammonium fumarate in said adjusted aqueous solution into monoammonium aspartate;
   (d) acidulating a solution containing said monoammonium aspartate by contacting with a cation exchanger which is at least partially in its acid form, at an elevated temperature of at least 50° C., whereby ammonium ions are transferred from said solution to said cation exchanger and protons are transferred from said cation exchanger to said solution thereby forming aspartic acid therein;
   (e) separating said aspartic acid containing aqueous solution from said ammonium ion-carrying cation exchanger;
   (f) separating said aspartic acid from said aqueous solution formed in step (e) by methods known per se;
   (g) regenerating said ammonium ion-carrying cation exchanger back to a cation exchanger which is at least partially in its acid form in a method that forms an ammonia source;
   (h) separating and reusing said converted cation exchanger in step (d); and
   (i) separating and reusing said ammonia source in step (a).

2. A process according to claim 1, wherein said ammonia source is selected from the group consisting of ammonia, ammonium carbonate and ammonium bicarbonate.

3. A process according to claim 1, wherein a raw material for said formation in step (a) is a carbohydrate, and a medium containing said carbohydrate is fermented by means of a fumaric acid-producing microorganism, whereby a fumarate containing fermentation liquor is formed.

4. A process according to claim 1, wherein said regeneration of said ammonium ion-carrying cation exchanger in step (g) uses $CO_2$ as a reagent.

5. A process for the production of asportic acid, comprising the steps of:
   (a) fermenting a carbohydrate-containing medium by means of a fumaric acid-producing microorganism, whereby a fumarate containing fermentation liquor is formed;
   (b) adjusting the composition of an aqueous solution containing diammonium fumarate obtained through a step of the present process to form a solution having a concentration of about 0.5M to about 2M ammonium fumarate and having a pH of about between 7 and 9;
   (c) enzymatically converting diammonium fumarate into monoammonium aspartate;
   (d) acidulating a solution containing said monoammonium aspartate by contacting with a cation exchanger which is at least partially in its acid form, at an elevated temperature of at least 50° C., whereby ammonium anions are transferred from said solution to said cation exchanger and protons are transferred from said cation exchanger to said solution forming aspartic acid therein;
   (e) separating said aspartic acid containing aqueous solution from said ammonium ion-carrying cation exchanger;
   (f) separating said aspartic acid from said aqueous solution formed in step (e) by methods known per se;
   (g) regenerating said ammonium ion-carrying cation exchanger with an aqueous solution of monoammonium fumarate, fumaric acid or mixture thereof obtained through a step of the present process, whereby protons are transferred from said solution to said cation exchanger and ammonium ions are transferred from said cation exchanger to said solution to form diammonium fumarate therein;
   (h) separating said cation exchanger from step (g) which is partially in its acid form and reusing said cation exchanger in step (d); and
   (i) decomposing said diammonium fumarate from step (g) to form monoammonium fumarate, fumaric acid or a mixture thereof and to form an ammonia source and reusing said decomposition products.

6. A process according to claim 5, wherein a base is used as a neutralizing agent in said fermentation.

7. A process according to claim 6, wherein said base is selected from the group consisting of ammonia and hydroxides, carbonates and bicarbonates of ammonium, alkali and alkaline earth metals.

8. A process according to claim 5, wherein an ammonia source is used as a reagent in said adjustment in step (b).

9. A process according to claim 5, wherein said diammonium fumarate from step (b) is decomposed in step (i) and said mohoammonium fumarate, fumaric acid or a mixture thereof is reused in step (g).

10. A process according to claim 5, wherein said diammonium fumarate from step (b) is enzymatically converted to monoammonium aspartate in step (c).

11. A process according to claim 5, wherein said diammonium fumarate formed in step (g) is decomposed in step (i) and said monoammonium fumarate, fumaric acid or a mixture thereof is reused in step (g).

12. A process according to claim 5, wherein said diammonium fumarate formed in step (g) is enzymatically converted to monoammonium aspartate in step (c).

13. A process according to claim 5, wherein a base of an alkaline earth metal is used as a neutralizing agent in said fermentation, fumarate of said alkaline earth is formed and is converted in step (b) into ammonium fumarate in a process that utilizes an ammonia source as a reagent and regenerates a base of an alkaline earth metal for reuse as a neutralizing agent.

14. A process according to claim 13, wherein said alkaline earth metal is calcium, said fumarate of alkaline earth metal is calcium fumarate and said base of an alkaline earth is calcium carbonate.

15. A process according to claim 14, wherein said calcium fumarate is purified prior to said conversion into ammonium fumarate in step (b).

16. A process according to claim 5, wherein said decomposition of diammonium fumarate in step (i) is effected by at least one method selected from the group consisting of:

(I) electrodialytic water splitting;

(II) contacting with an extractant under $CO_2$ pressure, whereby fumaric acid is extracted;

(III) acidulating by contacting with a cation exchanger which is at least partially in its acid form, whereby ammonium ions are transferred from said solution to said cation exchanger forming ammonium ion-carrying cation exchanger and protons are transferred from said cation exchanger to said solution forming monoammonium fumarate therein; and (IV) thermal decomposition.

17. A process according to claim 5, wherein said monoammonium fumarate is separated by methods known per se.

18. A process according to claim 17, wherein said monoammonium fumarate is separated by crystallization.

19. A process according to claim 5, wherein said monoammonium fumarate is purified before reuse.

20. A process according to claim 16 (III), wherein said ammonium ioncarrying cation exchanger is regenerated back to a cation exchanger which is at least partially in its acid form and reused.

21. A process according to claim 20, wherein said regeneration is effected using $CO_2$ as a reagent, a product is selected from the group consisting of ammonia, ammonium carbonate, ammonium bicarbonate and a mixture thereof is formed, separated and reused as an ammonia source.

22. A process according to claim 1, wherein fumaric acid is extracted from monoammonium fumarate solutions.

23. A process according to claim 1, wherein said separation of aspartic acid in step (e) is effected by crystallization and crystalline aspartic acid is separated from a mother liquor.

24. A process according to claim 23, wherein aspartic acid left in said mother liquor is recovered by adsorbing on a strong acid cation exchanger.

25. A process according to claim 24, wherein said aspartic acid-carrying cation exchanger is contacted with a solution of an aspartate salt, cations of said salt are adsorbed and aspartic acid is released into said solution.

26. A process according to claim 25, wherein said strong acid cation exchanger carrying cations of said aspartate salt is contacted with a solution of a reagent acid, whereby protons from said solution are adsorbed on said cation exchanger and said cations are released into said solution.

27. A process according to claim 26, wherein said reagent acid is fumaric acid and at least 80% of said cations are ammonium ions.

* * * * *